United States Patent [19]
Misaki et al.

[11] Patent Number: 4,791,057
[45] Date of Patent: Dec. 13, 1988

[54] HIGHLY SENSITIVE ENZYMATIC ASSAY METHOD
[75] Inventors: Hideo Misaki; Shigeru Ueda, both of Shizuoka, Japan
[73] Assignee: Toyo Jozo Kabushiki Kaisha, Shizuoka, Japan
[21] Appl. No.: 757,953
[22] Filed: Jul. 23, 1985
[30] Foreign Application Priority Data
Jul. 23, 1984 [JP] Japan ................... 59-151438
[51] Int. Cl.⁴ .............. C12Q 1/26; C12Q 1/32; C12Q 1/28
[52] U.S. Cl. ................... 435/26; 435/25; 435/28; 436/817
[58] Field of Search .............. 435/25, 26, 28, 192; 436/817

[56] References Cited
U.S. PATENT DOCUMENTS
4,230,797  10/1980  Boguslaski et al. ................ 435/7

OTHER PUBLICATIONS
Hurlock et al. (1956) Society of Experimental Biology and Medicine Proceedings, vol. 93, pp. 560–564.
Yamagouchi et al. (1981) Analytical Letters, vol. 14, No. B6, pp. 433–438.
Dolin, 1957 Science, vol. 225, pp. 557–573.
Blaedel et al. (1978), Analytical Chemistry, vol. 50, No. 8, pp. 1026–1032.

Primary Examiner—Robert J. Warden
Assistant Examiner—Jack Spiegel
Attorney, Agent, or Firm—Young & Thompson

[57] ABSTRACT

A highly sensitive quantitative assay method for a component which is $3\beta$-hydroxysteroid or 3-ketosteroid, in a specimen to be assayed, comprising causing this component in the specimen to take part in the cycling reaction

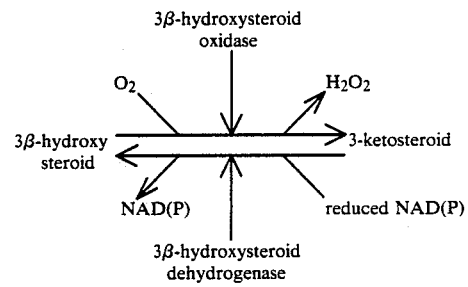

and measuring a detectable change in the reaction system. There is thus provided a $3\beta$-hydroxysteroid - 3-ketosteroid cycling reaction using $3\beta$-hydroxysteroid oxidase, which consumes $O_2$ and generates $H_2O_2$ and 3-ketosteroid, with a substrate of $3\beta$-hydroxysteroid, or $3\beta$-hydroxysteroid dehydrogenase, which consumes reduced NAD(P) and generate NAD(P) and $3\beta$-hydroxysteroid, with a substrate of 3-ketosteroid. Example of specimens are specimens which contain 3-hydroxysteroid or 3-ketosteroid, or which liberate or generate such a component. By proceeding at a rate of more than ten cycles per minute and measuring the amount of a detectable change in the reaction, the component in a specimen can easily and sensitively be detected with good accuracy.

8 Claims, 3 Drawing Sheets

HIGHLY SENSITIVE ENZYMATIC ASSAY METHOD

This invention relates to a quantitative assay method for a component in a specimen to be assayed, which component can be 3β-hydroxysteroid or 3-ketosteroid. More particularly the present invention relates to a highly sensitive enzymatic assay method which comprises reacting a component in the specimen with the components of the cycling reaction

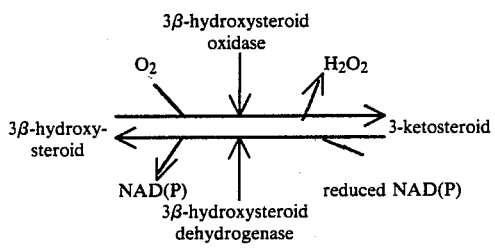

and measuring the amount of detectable change in the reaction system.

Enzymatic cycling assay methods such as NAD cycling, NADP cycling or CoA cycling are known. For example, alcohol dehydrogenase has been subjected to reaction with ethanol as a substrate in the presence of NAD to form reduced NAD which is oxidized to NAD by the action of malic dehydrogenase on a substrate of oxalacetate to constitute an NAD-reduced NAD cycling reaction. [*Jap. Biochem. Soc. Ed. "Experimental Methods in Biochemistry", Vol.* 5, "Research Methods in Enzymology", p. 121–135, Tokyo Kagaku Dojin Publishing Co., August 1975, Mori, A. Ed. "Manual of Assay Methods in Neuro-transmittance", p. 165–172, Ishiyaku Publishing Co., November 1979.]

Another method is known as follows:

In the above reaction, malic dehydrogenase is replaced by reduced NAD oxidase to constitute a cycling reaction wherein oxygen and reduced NAD are consumed and H₂O and NAD are generated [Institute for Phys. and Chem. Sci. Ed.: "Present and Future of Life-Science", p. 30–32, K. K. Creative Life Sci. Res. Assn., March 1981]. Hydroxysteroid is treated with hydroxysteroid dehydrogenase to reduce NAD to reduced NAD which is converted to NAD with the formation of formazane by the action of a transferase such as diaphorase in the presence of a tetrazolium salt to constitute the cycling reaction [Jap. Pat. Unexam. Publ. No. 56-144096].

Glutathione and dehydroascorbate are treated with glutathione dehydroascorbate oxido-reductase, thereby converting dehydroascorbate to ascorbate, which consumes oxygen and generates H₂O and dehydroascorbate by the action of ascorbate oxidase to constitute a cycling reaction. [Jap. Pat. Unexam. Publ. No. 56-151498.] NAD cycling wherein oxygen is consumed and hydrogen peroxide is generated by using reduced NAD oxidase is also known [Jap. Pat. Unexam. Publ. No. 56-78599].

As mentioned hereinabove, several kinds of cycling reaction systems have been reported, however, the one most frequently used, in which reduced NAD oxidase generates peroxide, suffers from the difficulty of purification, so that an accurate assay cannot be expected. Furthermore, in NAD cycling methods, complicated processes wherein excess NAD has to be decomposed by heating under alkaline conditions, and the said alkali then be neutralized, are required.

The concentration of steroid hormones in vital specimens is generally low and so direct assay by spectrophotometry has been difficult. In the prior art of assay methods, hydroxysteroid is treated with 3-hydroxysteroid dehydrogenase and NAD to generate reduced NAD which is colorimetrically measured at 350 nm. But this method is of low sensitivity and hence trace steroid horomones in serum, except cholesterol, cannot be measured.

We have now discovered a 3β-hydroxysteroid-3-ketosteroid cycling reaction using 3β-hydroxysteroid oxidase, which consumes O₂ and generates H₂O₂ and 3-ketosteroid, witth a substrate of 3β-hydroxysteroid, and furthermore 3β-hydroxysteroid dehydrogenase, which consumes reduced NAD(P) and generates NAD(P) and 3β-hydroxysteroid, with a substrate of 3-ketosteroid.

These reagents can be obtained at low cost and good quality, and moreover an effective cycling reaction can be achieved in spite of coexisting oxidatively active H₂O₂ and reductively active reduced NAD. Furthermore, we have found that in the cycling reaction, 3β-hydroxysteroid or 3-ketosteroid in a specimen is reacted with the remainder of the other components in the cycling reaction system consisting of 3β-hydroxysteroid, 3-ketosteroid, 3β-hydroxysteroid oxidase, 3β-hydroxysteroid dehydrogenase, NAD(P), reduced NAD(P), O₂ or H₂O₂, and that, by proceeding at a rate of more than ten cycles per minute and measuring the amount of a detectable change in the reaction, the target component in a specimen can easily and sensitively be detected with good accuracy.

An object of the present invention is to provide a simple and highly sensitive enzymatic assay method, without necessitating complicated pre-treatment as in known assay methods for 3β-hydroxysteroid or 3-ketosteroid in a specimen, by the use of a coenzyme cycling reaction.

These objects are achieved, according to the present invention, by the method which we have discovered, which comprises reacting a component in the specimen with the components of the cycling reaction

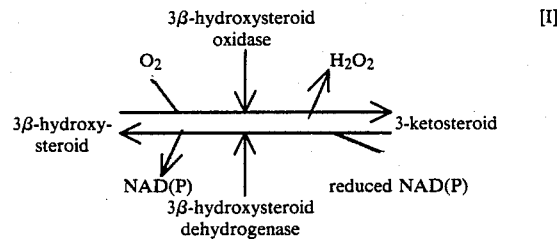

and measuring the amount of a detectable change in the reaction system.

Examples of specimens are specimens which contain 3β-hydroxysteroid or 3-ketosteroid, or which liberate or generate such a component. In the latter case, metabolic systems and biosynthetic systems of various steroid hormones, which are classified into, for example, androgens in male animals, estrogen or gestagen in female animals, and corticoid in both sexes, can be mentioned. An enzymatic activity which characterizes these systems, or the amount of 3β-hydroxysteroid or 3- ketosteroid, can be determined. Examples thereof are as follows:

3β-hydroxysteroid:
(1) Androgen:
pregnenolone, 17α-hydroxypregnenolone, dehydroepiandrosterone, androstene-3β,17β-diol, androstane-3β,17β-diol, Δ⁵-androsterone-3β,17α-diol, androstane-3β,11β-diol-17-one.
(2) Estrogen:
estradiol, estrone, estriol, equilin, equilenin, ethynylestradiol.

3-ketosteroid:
(1) Androgen:
progestreone, 17α-hydroxyprogesterone, testosterone, androstenedione.
(2) Corticoid:
corticosterone, cortisol, cortisone.

In an assay, 3β-hydroxysteroid oxidase, 3β-hydroxysteroid dehydrogenase and reduced NAD(P) are added to a specimen which contains any one of the above components to be asssayed.

The concentration of the substrate, i.e. 3β-hydroxysteroid or 3-ketosteroid, can optionally be adjusted to be 5 nM-30 μM/5-20 μl. The reaction temperature can be a temperature at which a smooth cycling reaction proceeds, and is preferably 37° C. The reaction time will vary depending on the substrate concentration, the enzyme concentration and the reaction temperature, and is usually more than one minute, preferably 2-10 minutes.

An example of 3β-hydroxysteroid dehydrogenease is a commercially available product obtained from *Pseudomonas testeroni* (Sigma Chem. Co., U.S.A.) The amount to be used is more than 0.05 unit/ml in one reaction, preferably 2-4 units/ml.

An example of 3β-hydroxysteroid oxidase is a commercially available enzyme, generally known as cholesterol oxidase (EC 1.1.3.6), which is produced from a microorganism Streptococcus, Brevibacterium, Schizophylum, Corynebacterium, Cellulomonas, Arthrobacter, Nocardia or Mycobacterium. The amount of the enzyme used is more than 0.2 unit/ml, preferably 10-30 unit/ml.

The amount of reduced NAD(P) to be added is generally a stoichiometric excess as compared with the substrate to be assayed, and is preferably 0.1-2.0 mM.

The above concentrations of substrate, enzyme and the other necessary component in the reaction system can optionally be varied and are not limited.

The cycling reaction [I] of the present invention can be illustrated in the following reaction schema for 3β-hydroxysteroid, 3-ketosteroid, 3β-hydroxysteroid dehydrogenase, 3β-hydroxysteroid oxidase, NAD(P), reduced NAD(P), O₂ and H₂O₂.

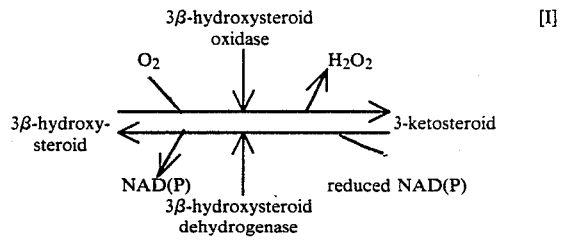

In the reaction [I], one mole of 3β-hydroxysteroid is converted with the consumption of one mole of O₂, generally dissolved oxygen, to one mole of 3-ketosteroid with the generation of one mole of H₂O₂ by the action of 3β-hydroxysteroid oxidase to constitute the 3β-hydroxysteroid oxidase reaction system. Then one mole of 3-ketosteroid is further converted by the action of 3β-hydroxysteroid dehydrogenase in the presence of one mole of reduced NAD(P) to one mole of 3β-hydroxysteroid with the generation of one mole of NAD(P), to constitute the 3β-hydroxysteroid dehydrogenase reaction system. Furthermore, the thus-generated 3β-hydroxysteroid is converted to 3-ketosteroid to constitute the 3β-hydroxysteroid oxidase reaction system, thereby constituting the 3β-hydroxysteroid-3-ketosteroid cycling reaction. The said cycling reaction [I] proceeds in the presence of the six components, 3β-hydroxysteroid, 3-ketosteroid, 3β-hydroxysteroid oxidase, 3β-hydroxysteroid dehydrogenase, reduced NAD(P) and O₂; however, 3β-hydroxysteroid and 3-ketosteroid can be formed from each other by a cycling reaction, and therefore either one thereof can be used as desired.

Furthermore, in the cycling reaction [I], H₂O₂ and reduced NAD can be linked to form NAD, wherein one mole of H₂O₂ and one mole of reduced NAD are consumed to form two mols of H₂O and one mole of NAD by the action of NAD peroxidase (EC 1.11.1.1) [*J. Biol. Chem.*, 225: 557, 1957] as shown by the following reaction:

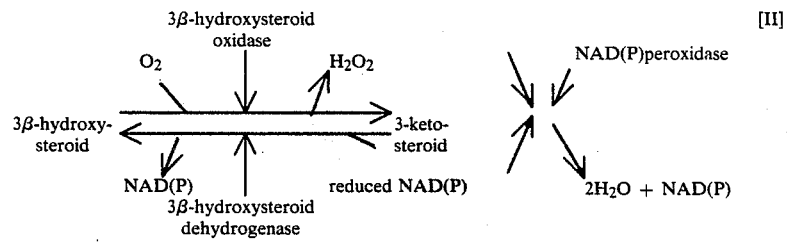

In cycling reaction [II], H₂O₂ generated in cycling reaction [I] is consumed with reduced NAD(P) to form NAD(P), and so two moles of reduced NAD(P) are consumed in one cycle of cycling reaction [II], which provides twofold more rapid changes in the amount of reduced NAD(P) and a more highly sensitive assay method.

Alternatively, NAD(P) can be converted by another dehydrogenase (herein called a second dehydrogenase) and its substrate, to reduced NAD(P), to constitute an NAD(P) cycling reaction consisting of NAD(P), the second dehydrogenase and a substrate thereof. The said NAD(P) cycling can be linked with cycling reaction [I] as illustrated by the following reaction:

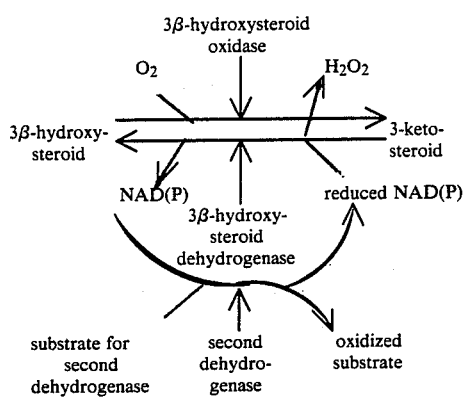

For example, a component in the specimen (shown as →) and a component which constitutes cycling reaction [I] (shown as ) can be illustrated as follows:

(a) Component in specimen; 3β-hydroxysteroid:

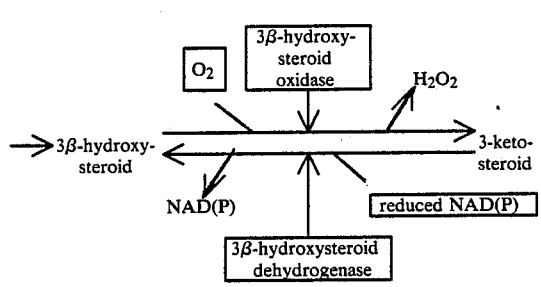

In cycling reaction [Ia], if the component in the specimen is 3β-hydroxysteroid, then 3β-hydroxysteroid oxidase, 3β-hydroxysteroid dehydrogenase, $O_2$ and reduced NAD(P) are used for the components which constitute the cycling reaction. 3β-hydroxysteroid oxidase is the substrate, which consumes one mole of 3β-hydroxysteroid and $O_2$ and generates one mole of $H_2O_2$ and 3-ketosteroid. Furthermore, 3β-hydroxysteroid dehydrogenase acts on a substrate of 3-ketosteroid to consume one mole of 3-ketosteroid and reduced NAD(P) and generate one mole of 3β-hydroxysteroid and NAD(P), thereby to complete the 3β-hydroxysteroid-3-ketosteroid cycling reaction. In the reaction, $O_2$ can be supplied by dissolved oxygen in the system and so 3β-hydroxysteroid oxidase, 3β-hyroxysteroid dehydrogenase and reduced NAD(P) should be supplied in excess amounts as reagents for the assay. The amount of 3β-hydroxysteroid in the specimen is not limited but will naturally be diluted if at high concentration.

The amount of 3β-hydroxysteroid oxidase and 3β-hydroxysteroid dehydrogenase depends on the amount of 3β-hydroxysteroid in the specimen and is usually more than 0.2 unit/ml per one test, preferably 10–30 units/ml for 3β-hydroxysteroid oxidase and more than 0.05 unit/ml per one test, preferably 2–4 units/ml for 3β-hydroxysteroid dehydrogenase. The amount of reduced NAD(P) can be more than the product of the amount of 3β-hydroxysteroid in the specimen times the number of cycles, and is generally in stoichiometric excess of the amount of 3β-hydroxysteroid, for example more than 50 times, preferably 100–10,000 times. The magnitude of the detectable change after the cycling reaction is completed can be determined by the amount of consumed $O_2$ or reduced NAD(P) or generated $H_2O_2$. As shown in cycling reaction [II] hereinbefore, the generated $H_2O_2$ and consumed reduced NAD(P) can be linked for highly sensitive assaying. In this linked reaction, NAD(P) peroxidase is used, in general, in an amount more than 0.5 unit per one test, preferably 1–20 units. The magnitude of the detectable change can preferably be determined by measuring the consumed reduced NAD(P).

(b) Component in specimen; 3-ketosteroid:

The schema is illustrated in the following reaction:

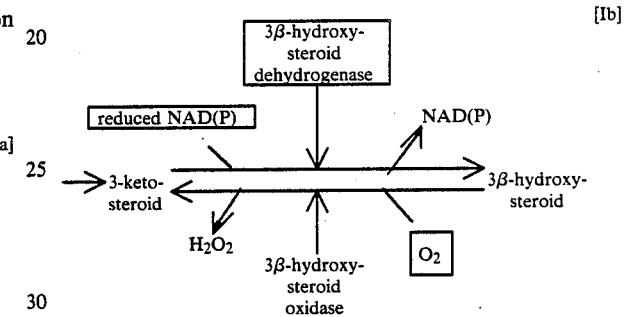

Any of 3β-hydroxysteroid oxidase, 3β-hydroxysteroid dehydrogenase, $O_2$ and reduced NAD(P) can be the component which completes cycling reaction [Ib]. In this reaction, 3-ketosteroid-3β-hydroxysteroid cycling is characterized by consuming one mole of 3-ketosteroid and reduced NAD(P) to generate one mole of NAD(P) and 3β-hydroxysteroid, then by consuming one mole of 3β-hydroxysteroid and $O_2$ to generate one mole of $H_2O_2$ and 3-ketosteroid. $O_2$ can be supplied by dissolved oxygen and so 3β-hydroxysteroid oxidase, 3β-hydroxysteroid dehydrogenase and reduced NAD(P) are simply added in stoichiometric excess. The amount of 3β-hydroxysteroid dehydrogenase and of 3β-hydroxysteroid oxidase is generally more than 0.05 unit/ml for the former, and more than 0.2 unit/ml for the latter, preferably 10–30 units/ml for 3β-hydroxysteroid dehydrogenase and 2–4 units/ml for 3β-hydroxysteroid oxidase. The amount of reduced NAD(P) to be used is determined by the product of the amount of 3-ketosteroid in the specimen times the number of cycles, and is in general, in stoichiometric excess as compared with the amount of 3-ketosteroid, for example more than 50 times, preferably 100–10,000 times. The magnitude of the detectable change after completion of the cycling reaction can be determined by consumed oxygen or reduced NAD(P) or generated $H_2O_2$. High sensitivity of assay can be achieved by using NAD(P) peroxidase as hereinbefore illustrated.

Hereinafter, an assay method using a second dehydrogenase and its substrate as illustrated in reaction [III] hereinbefore will be explained.

The cycling reaction is illustrated by the following reaction:

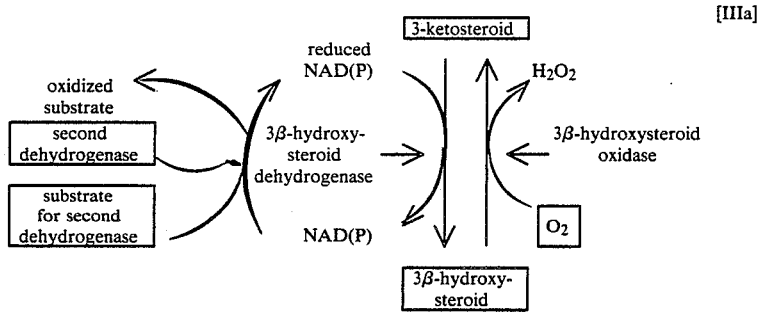

[IIIa]

Any one of 3-ketosteroid or 3β-hydroxysteroid dehydrogenase, 3β-hydroxysteroid oxidase, O₂, any one of NAD(P) or reduced NAD(P), the second dehydrogenase and the substrate for the second dehydrogenase are used as the components which complete the cycling reaction [IIIa]. In this reaction, the second dehydrogenase acts on NAD(P), and one mole of NAD(P) and the substrate for the second dehydrogenase are consumed to generate one mole of oxidative product and reduced NAD(P), then the reduced NAD(P) is used in the 3-ketosteroid-3β-hydroxysteroid cycling reaction. 3β-hydroxysteroid dehydrogenase acts on the generated reduced NAD(P) and an equimolar ratio of 3-ketosteroid to generate one mole of NAD(P) and 3β-hydroxysteroid, and then one mole of 3β-hydroxysteroid and O₂ are consumed by the action of 3β-hydroxysteroid oxidase to form one mole of $H_2O_2$ and 3-ketosteroid. In this reaction, O₂ can be supplied from dissolved oxygen in the mixture, as also 3β-hydroxysteroid oxidase, 3β-hydroxysteroid dehydrogenase and NAD(P) [or reduced NAD(P)], and the second dehydrogenase and its substrate should be supplied as reagents for assaying in excess amounts. The magnitude of the detectable change can be determined by measuring consumed O₂ or generatd $H_2O_2$.

The second dehydrogenase used in the cycling reaction [IIIa] can be an enzyme which catalyzes a reaction on a substrate for the said dehydrogenase and NAD(P) to form oxidative products of the said substrate and reduced NAD(P), and is illustrated as follows:

(a) Dehydrogenase; D-arabitol dehydrogenase (A Dase) (EC 1.1.1.11) and its substrate: D-arabitol:

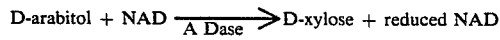

(b) Lactate dehydrogenase (LDH) (EC 1.1.1.27) and L-lactate:

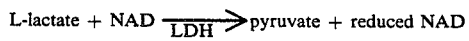

(c) Malate dehydrogenase (decarboxylating) (MDH) (EC 1.1.1.28) and L-malate:

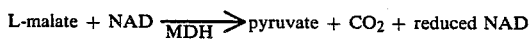

(d) Glucose dehydrogenase (GDH) (EC 1.1.1.47) and glucose:

(e) Formate dehydrogenase (FDH) (EC 1.2.1.2) and formate:

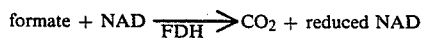

(f) Galactose dehydrogenase (Gal DH) (EC 1.1.1.48) and D-galactose:

-continued

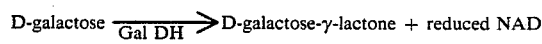

In cycling reaction [Id], NAD in the specimen is converted to reduced NAD by the action of the second dehydrogenase in the presence of a substrate therefor to take part in the NAD cycling reaction, then the thus-generated reduced NAD participates in the same cycling reaction as in [Ic] hereinbefore.

The amount of reagents used in cycling reaction [IIIa] can be in stoichiometric excess of the amount of NAD(P) or reduced NAD(P). Furthermore, the said NAD(P) cycling reaction can be linked by the action of NAD(P) peroxidase as illustrated in cycling reaction [II].

Then any one of the components 3β-hydroxysteroid or 3-ketosteroid in the specimen or a specimen which liberates or generates the said component is measured and the said component or specimen can be assayed based on the above cycling reaction [Ia], [Ib] or [III], or [IIIa], or [II]. In the reaction, the number of cycles is more than 10, and so the amount of reagents used is preferably in molar excess of the number of cycles. Furthermore, trace amounts of specimen or diluted specimen are advantageously used.

The reaction medium can be a stable pH buffer solution, generally weakly acidic to weakly alkaline. For example, a phosphate buffer of pH 6.5–8.5, a tris-HCl buffer, an imidazole-HCl buffer, a dimethylglutarate-NaOH buffer or a PIPES-NaOH buffer can be used. The reaction proceeds generally at 37° C. for more than one minute.

Cycling reaction [I] proceeds usually at a rate of more than 50 cycles per minute, although this value varies depending on the amount of enzyme used or its Km value, and so the amount of enzyme and reagents can be provided preferably for more than 60 cycles/min. of reaction.

Next, the magnitude of a detectable change in the reaction is measured after the reaction proceeds, and the said detectable change is the quantity of component, which consumes or generates one molar ratio of the component, in one reaction cycle wherein one mole of 3β-hydroxysteroid or 3-ketosteroid is consumed or generated during cycling reaction [I]. The preferred component to be measured is consumed O₂ or reduced NAD(P), or generated $H_2O_2$.

The amount of consumed O₂ can usually be determined by the value of electro-chemical changes using an oxygen electrode. The amount of consumed reduced NAD(P) can be determined by subtracting the amount of reduced NAD(P) remaining at the end of the reaction from the initial amount of reduced NAD(P). Measuring these amounts of reduced NAD(P) can be done by various known assay methods. For example, the specific absorbency of reduced NAD(P) and the non-specific absorbency of NAD(P) can be measured. Since NAD(P) has its specific absorption maximum at 260 nm and reduced NAD(P) at 260 nm and 340 nm, the absorbency at 320–360 nm, preferably at 340 nm is measured for assaying reduced NAD(P).

Another assay method for reduced NAD(P) is a colorimetric assay using an electron transport chromogen having an electron acceptor from reduced NAD(P). Examples of electron transport chromogens are tetrazolium salts such as 3-(p-iodophenyl)-2-(p-nitrophenyl)-5-phenyl-2H-tetrazolium chloride, 3-(4,5-dimethyl-2-thiazolyl)-2,5-diphenyl-2H-tetrazolium bromide, 3,3'-(4,4'-biphenylene)-bis(2,5-diphenyl-2H-tetrazolium chloride), 3,3'-(3,3'-dimethoxy-4,4'-biphenylene)-bis[2-(p-nitrophenyl)-5-phenyl-2H-tetrazolium chloride] (=nitro-tetrazolium: NTB), 3,3'-(3,3'-dimethoxy-4,4'biphenylene)-bis[2,5-bis(p-nitrophenyl)-2H-tetrazolium chloride], 3,3'-(3,3'-dimethoxy-4,4'-biphenylene)-bis(2,5-diphenyl-2H-tetrazolium chloride), and 2,6-dichlorophenol-indophenol. A preferred example is a combination of water-soluble tetrazolium salt and diaphorase or phenazinemethosulfate. These electron transport chromogens are electron acceptors for reduced NAD(P) to form a colored formazane pigment, and the thus formed pigment is colorimetrically measured at the maximum absorption thereof such as 500–550 nm.

A further assay method for reduced NAD(P) is fluorometry wherein reduced NAD(P) is treated with diaphorase in the presence of a fluorescent reagent such as resazulin. For assaying reduced NAD(P) in cycling reaction [I], $N_2O_2$ should preferably be decomposed and removed by catalase. NAD(P) peroxidase (EC 1.11.1.1) can be added to cycling reaction [I] for a doubly sensitive assay as illustrated in reaction system [II] herinbefore. Generated $H_2O_2$ can be measured as an electro-chemical change by using a hydrogen peroxide electrode, or as a detectable product by reacting with an indicator and $H_2O_2$. Examples of indicators are reagents which can be measured by spectrophotometric means, color indicators, fluorescent reagents or luminescent reagents.

The present invention is thus a novel assay method for 3β-hydroxysteroid or 3-ketosteroid in a specimen by means of a cycling reagent of 3β-hydroxysteroid-3-ketosteroid, substrate for a coupling of 3β-hydroxysteroid dehydrogenase and 3β-hydroxysteroid oxidase, at a rate of more than 10 cycles per minute, wherein a component, namely 3β-hydroxysteroid or 3-ketosteroid in a specimen such as serum or urine, is measured with good accuracy and high sensitivity of 100–1,000 times/10 minutes as compared with known methods.

The following examples illustrate the present invention but are not to be construed as limiting.

The results of the examples are shown in the accompanying drawings, in which.

EXAMPLE 1

The following reaction mixture is used for assay:
50 mM phosphate buffer (pH 7.5)
3β-hydroxysteroid oxidase (Toyo Jozo Co., produced from Streptomyces): 20 units/ml
3β-hydroxysteroid dehydrogenase (Sigma Chem. Co., produced from *Pseudomonas teststeroni*): 2 units/ml
1.5 mM reduced NAD (NADH$_2$)
0.1% Triton X-100

The above reaction mixture (0.5 ml) was introduced into a small test tube and preincubated at 37° C. Specimens (0 μl) containing pregnenolone (0, 5, 10, 15 and 20 μM, respectively) were added thereto, and the mixture was incubated for exactly 10 minutes. The reaction was stopped by adding 2% sodium dodecyl sulfate (SDS) (2.5 ml). Changes of absorbency of the reaction mixture were measured at 340 nm.

Figure 1:
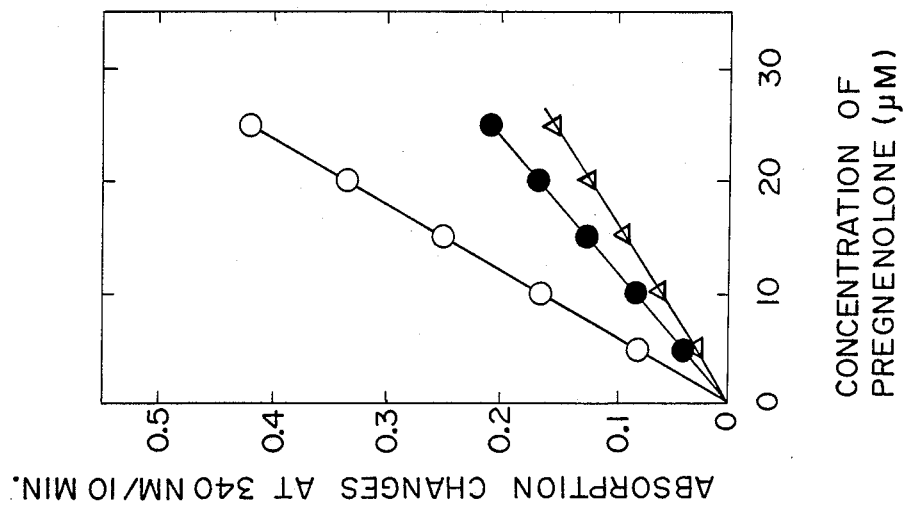

The results are shown in FIG. 1 (●—●) with good quantitativity. The cycling ratio in this example was 80 cycles/min. Reduced NAD in the above reaction mixture was replaced by reduced NADP, and the same process as above was followed to obtain the good quantitative results shown in FIG. 1 (△—△). Furthermore, NADH$_2$-peroxidase (9 units/ml) was added to the reaction mixture being reduced NAD hereinabove, and the material was assayed as above. The results are shown in FIG. 1 (o—o) with two times greater absorbency.

EXAMPLE 2

Reaction mixture:
50 mM phosphate buffer (pH 8.0)
3β-hydroxysteroid oxidase: 20 units/ml
3β-hydroxysteroid dehydrogenase: 4 units/ml
0.2 mM reduced NAD (NADH$_2$)
0.1% Triton X-100

The above reaction mixture (1.0 ml) was introduced into a quartz cell (1.0 ml) and was set in a spectrophotometer assembled with a constant temperature cell-holder at 37° C.

Figure 2:
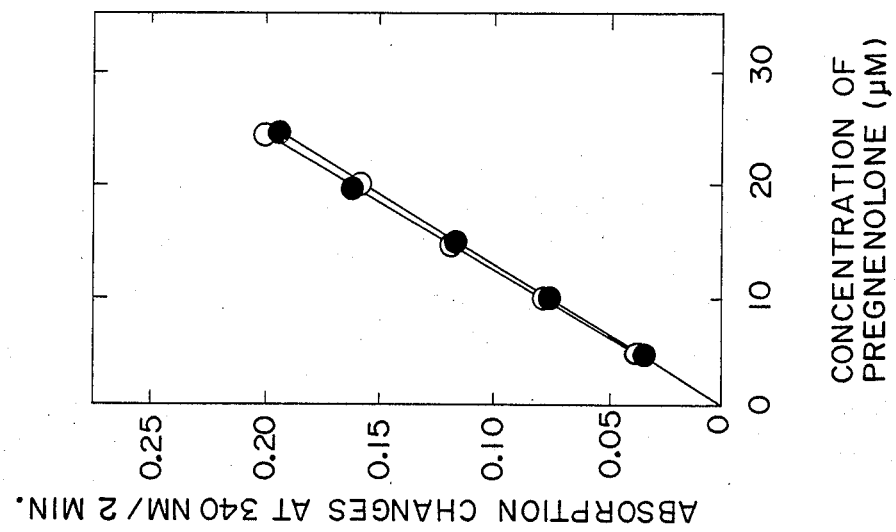
FIGS. 1 and 2 are the quantitative assay curves for pregnenolone.

Specimens (20 μl) containing pregnenolone (0, 5, 10, 15, 20 and 25 μM, respectively) were added thereto and each mixture was incubated at 37° C. Changes of absorbency each 2 minutes from 2 to 4 minutes after starting the reaction were measured at 340 nm. The results are shown in FIG. 2 (o—o), in which displays good linearity as to the amount of pregnenolone and absorbency. The cycling ratio in this example was 65 cycles/min.

Human serum, to which pregnenolone was added to the same concentration as above, was used for assay in the same way to obtain the results as shown in FIG. 2 (●—●) with good quantitativity.

EXAMPLE 3

Figure 3:
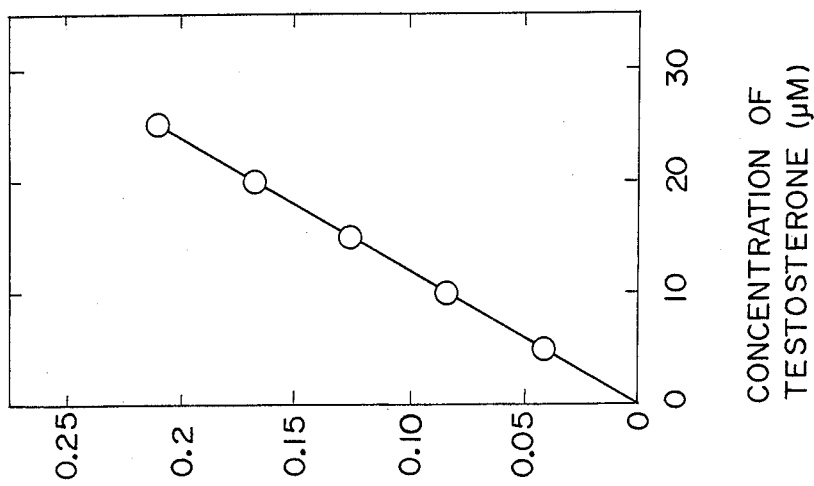
FIG. 3 is the quantitative assay curve for testosterone.

Solutions (10 μl) containing testosterone (0, 5, 10, 15 and 20 μM, respectively) were added to a reaction mixture (0.5 ml) of the same composition as in Example 1 and treated the same as in Example 1. The results are shown in FIG. 3, which shows that good quantitativity was obtained in the case of testosterone.

EXAMPLE 4

Figure 4:
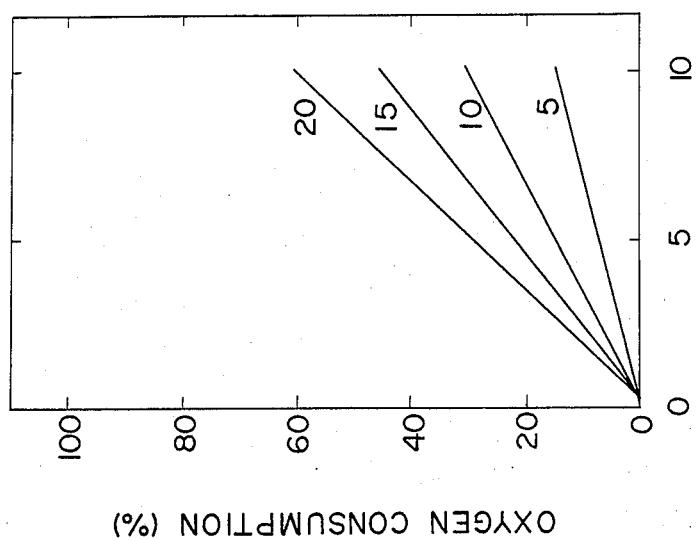
FIG. 4 is the quantitative assay curve for pregnenolone.

The reaction mixture (1.0 ml) of Example 2 was introduced into a reaction vessel assembled with a Galvani type oxygen electrode and the mixture was preincubated at 37° C. Solutions (10 μl) containing pregnenolone (0, 5, 10, 15 and 20 μM, respectively) were added thereto and the mixtures were incubated at 37° C. for 10 minutes. Then oxygen consumption was measured. The results are shown in FIG. 4 and prove the high sensitivity of the present method.

EXAMPLE 5

Figure 5:
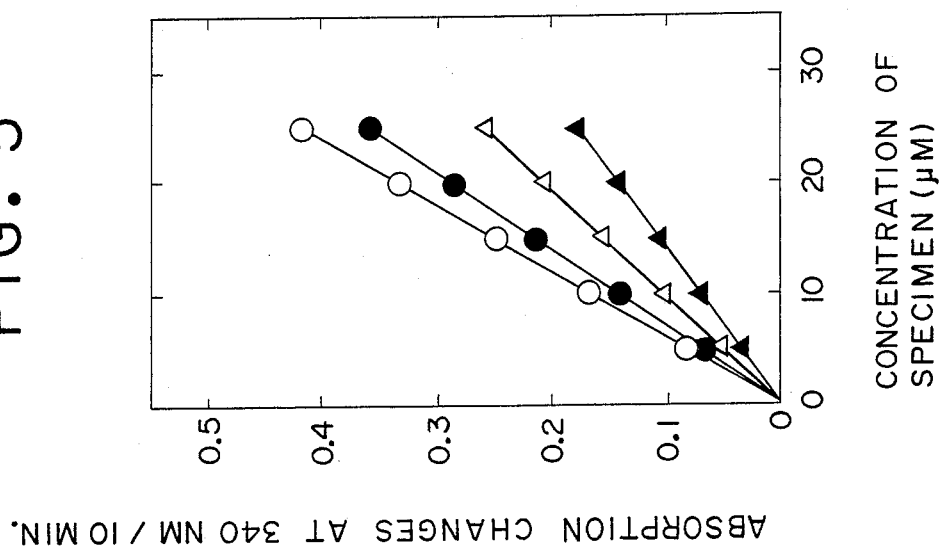
FIG. 5 is the quantitative assay curve for pregnenolone, androstenedione, dehydroisoandrosterone and androstene-3β,17β-diol.

Specimens (20 μl) containing pregnenolone, androsterone, dehydroisoandrosterone or androstenedione-3β,17β-dione (0, 5, 10, 15, 20 and 25 μM, respectively) were added to the reaction mixture of Example 1, and the changes of absorbency were measured after treatment the same as in Example 1. The results are shown in FIG. 5, wherein o—o: pregnenolone, ●—●: androsterone, ∆—∆: dehydroisoandrosterone and ▲—▲: androsterone-3β,17β-diol.

EXAMPLE 6

Figure 6:
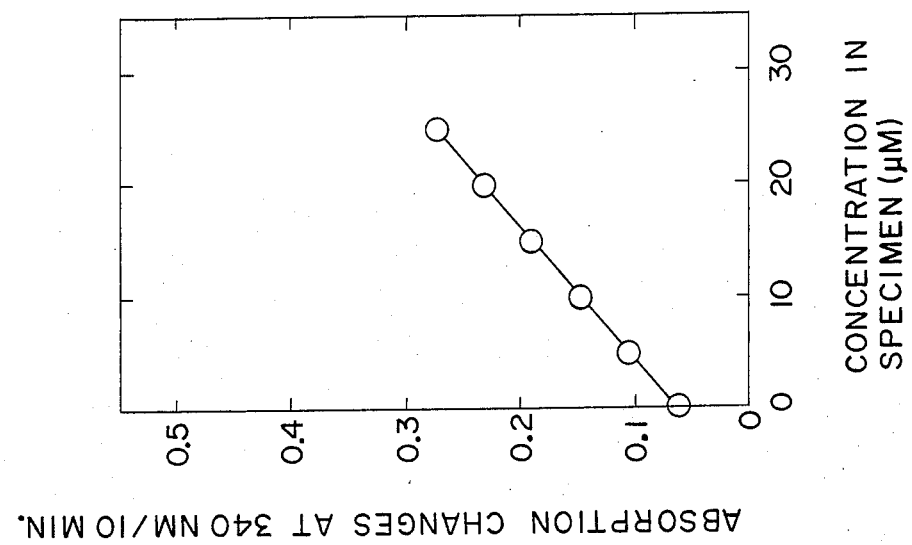
FIG. 6 is the quantitative assay curve for pregnenolone.

Human serum specimens were prepared by adding pregnenolone at concentrations of 0, 5, 10, 15, 20 and 25 μM, respectively. The specimens (20 μl) were added to the reaction mixture in Example 1, and treated as in Example 1 to measure pregnenolone. The results are shown in FIG. 6 and demonstrate good recovery.

What is claimed is:

1. A quantitative enzymatic assay method for 3β-hydroxysteroid or 3-ketosteroid in a specimen to be assayed, comprising the steps of:

causing at least one component selected from the group consisting of 3β-hydroxysteroid and 3-ketosteroid, and contained in a specimen to be assayed, to take part in a cycling reaction system as follows

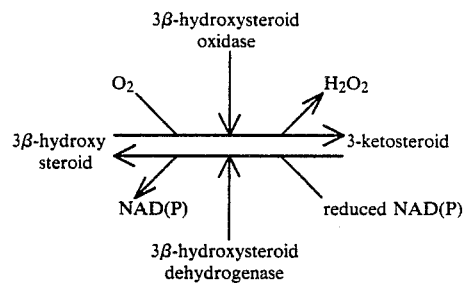

and measuring an amount of a compound consumed or generated in said cycling reaction system, and deriving a quantitation for either 3β-hydroxysteroid or 3-ketosteroid based on said measurement.

2. An assay method according to claim 1, wherein NAD peroxidase, which catalyzes a reaction consuming one moled of $H_2O_2$ and one mole of reduced NAD and generates two moles of $H_2O$ and one mole of NAD, is used to react said $H_2O_2$ and said reduced NAD(P) in said cycling reaction system and an amount of reduced NAD(P) consumed is measured.

3. An assay method according to claim 1, wherein said NAD(P) generated in said cycling reaction system is subjected to a second cycling reaction contained within said cycling reaction system, wherein a second dehydrogenase and a substrate for said second dehydrogenase are added to said cycling reaction system, said substrate and said generated NAD(P) reacting to oxidize said substrate and reconvert said NAD(P) to reduced NAD(P), said second dehydrogenase catalyzing said reconversion of said generated NAD(P).

4. An assay method according to claim 1, wherein the amount of $O_2$ consumed in said cycling reaction system is measured.

5. An assay method according to claim 1, wherein the amount of $H_2O_2$ generated in said cycling reaction system is measured.

6. An assay method according to claim 1, wherein said detectable change is the amount of consumed reduced NAD(P).

7. An assay method according to claim 1, wherein said 3β-hydroxysteroid dehydrogenase is an enzyme produced by *Pseudomonas teststeroni*.

8. An assay method according to claim 1, wherein said 3β-hydroxysteroid oxidase is an enzyme produced by a microorganism of genus selected from the group consisting of Streptomyces, Brevibacterium, Schizophylum, Corynebacterium, Cellulomonas, Arthrobacter, Mycobacterium and Nocardia.

* * * * *